(12) United States Patent
Liang et al.

(10) Patent No.: US 10,874,617 B2
(45) Date of Patent: Dec. 29, 2020

(54) ORAL PHARMACEUTICAL COMPOSITIONS OF MESALAZINE

(71) Applicant: Ferring B.V., Hoofddorp (NL)

(72) Inventors: Alfred Chi Yeh Liang, Rahway, NJ (US); Venkataramana Dingari, Franklin Park, NJ (US)

(73) Assignee: FERRING B.V., Hoofddorp (NL)

( * ) Notice: Subject to any disclaimer, the term of this patent is extended or adjusted under 35 U.S.C. 154(b) by 3 days.

(21) Appl. No.: 16/094,644

(22) PCT Filed: Apr. 18, 2017

(86) PCT No.: PCT/US2017/028067
§ 371 (c)(1),
(2) Date: Oct. 18, 2018

(87) PCT Pub. No.: WO2017/184566
PCT Pub. Date: Oct. 26, 2017

(65) Prior Publication Data
US 2019/0105275 A1    Apr. 11, 2019

Related U.S. Application Data

(60) Provisional application No. 62/324,416, filed on Apr. 19, 2016.

(51) Int. Cl.
| | | |
|---|---|---|
| *A61K 9/20* | (2006.01) | |
| *A61K 9/28* | (2006.01) | |
| *A61K 9/48* | (2006.01) | |
| *A61K 31/606* | (2006.01) | |
| *A61P 1/00* | (2006.01) | |
| *A61K 9/00* | (2006.01) | |

(52) U.S. Cl.
CPC .......... *A61K 9/2077* (2013.01); *A61K 9/2846* (2013.01); *A61K 9/2866* (2013.01); *A61K 9/2886* (2013.01); *A61K 9/4808* (2013.01); *A61K 31/606* (2013.01); *A61K 9/0053* (2013.01); *A61K 9/2027* (2013.01); *A61K 9/2054* (2013.01); *A61K 9/2095* (2013.01); *A61P 1/00* (2018.01)

(58) Field of Classification Search
None
See application file for complete search history.

(56) References Cited

U.S. PATENT DOCUMENTS

| | | |
|---|---|---|
| 2001/0024658 A1 | 9/2001 | Chen et al. |
| 2002/0034541 A1 | 3/2002 | Valducci |
| 2003/0152627 A1* | 8/2003 | Beckert .............. A61K 9/2081 424/470 |
| 2007/0060552 A1 | 3/2007 | Ekwuribe et al. |
| 2008/0286344 A1 | 11/2008 | Darmuzey et al. |
| 2012/0093939 A1 | 4/2012 | Payne et al. |
| 2013/0017262 A1 | 1/2013 | Mullen et al. |
| 2013/0022677 A1 | 1/2013 | Mullen et al. |
| 2014/0178468 A1 | 1/2014 | Shear et al. |
| 2014/0271859 A1 | 9/2014 | Loughlin et al. |
| 2015/0056275 A1* | 2/2015 | Bowe .................. A61K 9/2018 424/461 |
| 2015/0126462 A1 | 5/2015 | Waetzig et al. |
| 2015/0164920 A1 | 6/2015 | Soler Ranzani et al. |
| 2016/0045442 A1 | 2/2016 | Khera et al. |
| 2016/0317557 A1 | 11/2016 | Watzig et al. |
| 2017/0027924 A1 | 2/2017 | Watzig et al. |

FOREIGN PATENT DOCUMENTS

| | | | |
|---|---|---|---|
| CN | 104257669 A | | 1/2015 |
| CN | 105687158 B | * | 6/2019 |
| WO | WO-2004/066910 A2 | | 8/2004 |
| WO | WO-2013/134348 A1 | | 9/2013 |
| WO | WO-2013134348 A1 | * | 9/2013 ........... A61K 31/606 |

OTHER PUBLICATIONS

Nugent SG et al. "Intestinal luminal pH in inflammatory bowel disease: possible determinants and implications for therapy with aminosalicylates and other drugs," Gut. vol. 48. (2001) pp. 571-577 URL: https://www.ncbi.nlm.nih.gov/pmc/articles/PMC1728243/.

* cited by examiner

*Primary Examiner* — Celeste A Roney
(74) *Attorney, Agent, or Firm* — Foley & Lardner LLP (57) ABSTRACT

Described herein are pharmaceutical compositions for the oral administration of mesalazine, as well as methods of making such pharmaceutical compositions, and therapeutic methods for using them. The compositions comprise delayed-immediate release and delayed-extended release formulation of mesalazine.

22 Claims, 8 Drawing Sheets

ORAL PHARMACEUTICAL COMPOSITIONS OF MESALAZINE

RELATED APPLICATIONS

The application claims the priority benefits of U.S. provisional application 62/324,416, filed Apr. 19, 2016, the entire contents of which are incorporated herein by reference.

FIELD

Described herein are pharmaceutical compositions for the oral administration of mesalazine, as well as methods of making such pharmaceutical compositions, and therapeutic methods for using them.

BACKGROUND

Mesalazine (also known as 5-amino-2-hydroxybenzoic acid, 5-ASA, or mesalamine) is an anti-inflammatory drug used to treat inflammatory bowel disease, such as ulcerative colitis and mild-to-moderate Crohn's disease. The activity of mesalazine against these conditions is primarily local, and so mesalazine typically is administered by a dosage form and route of administration that will deliver the mesalazine to a desired site of activity, such as the colon or small bowel, for example. Thus, mesalazine is available in various dosage forms, including oral and rectal formulations, and in formulations having different release mechanisms, such as time-dependent/pH-independent release mechanisms (such as Pentasa®) and pH-dependent release mechanisms (such as Asacol® or Delzicol®). Currently available oral dosage forms of mesalazine include single tablets, beads, and capsules.

However, there remains a need for pharmaceutical compositions for the oral administration of mesalazine with different release profiles, because patients suffering from inflammatory bowel disease exhibit gastrointestinal tract symptoms that vary in location and degree.

SUMMARY

In one aspect, provided herein is a unit dose pharmaceutical product for the oral administration of mesalazine to a subject, comprising (a) a plurality of delayed-immediate release minitablets comprising a compressed matrix comprising mesalazine provided with a pH-dependent enteric coating, wherein the delayed-immediate release minitablets selectively release mesalazine in the distal ileum; and (b) a plurality of delayed-extended release minitablets comprising a compressed matrix comprising mesalazine provided with an inner pH-independent extended release coating and an outer pH-dependent enteric coating, wherein the delayed-extended release minitablets selectively release mesalazine in the colon; wherein the relative amounts of (a) and (b) in the unit dose pharmaceutical product are such that from 10 to 90% w/w of the mesalazine provided in the unit dose pharmaceutical is present in the delayed-extended release minitablets of (b), and the total amount of mesalazine in the unit dose pharmaceutical product is from about 0.4 to about 6 g.

In some embodiments, the delayed-immediate release minitablets release mesalazine at a pH of about 5.5 or greater. In some embodiments, when subject to in vitro dissolution testing according to USP Type 1 Basket at 37° C. and 100 rpm in 500 mL dissolution medium of pH 1.2 buffer for 2 hours, followed by pH 4.5 buffer for 2 hours, followed by pH 6.8 buffer for 2 hours, the delayed-immediate release minitablets exhibit substantially no release of mesalazine at pH 1.2 and pH 4.5, and release substantially all mesalazine within 120 minutes at pH 6.8. In some embodiments, when subject to in vitro dissolution testing according to USP Type 1 Basket at 37° C. and 100 rpm in 500 mL dissolution medium of pH 1.2 buffer for 2 hours, followed by pH 4.5 buffer for 2 hours, followed by pH 6.8 buffer for 2 hours, the delayed-immediate release minitablets exhibit substantially no release of mesalazine at pH 1.2 and pH 4.5, and release substantially all mesalazine within 90 minutes at pH 6.8.

In some embodiments, the delayed-immediate release minitablets release mesalazine at a pH of about 5.5 or greater. In some embodiments, when subject to in vitro dissolution testing according to USP Type 1 Basket at 37° C. and 100 rpm in 500 mL dissolution medium of pH 1.2 buffer for 2 hours, followed by pH 4.5 buffer for 2 hours, followed by pH 7.0 buffer, the delayed-immediate release minitablets exhibit substantially no release of mesalazine at pH 1.2 and pH 4.5, and release substantially all mesalazine within 120 minutes at pH 7.0. In some embodiments, when subject to in vitro dissolution testing according to USP Type 1 Basket at 37° C. and 100 rpm in 500 mL dissolution medium of pH 1.2 buffer for 2 hours, followed by pH 4.5 buffer for 2 hours, followed by pH 7.0 buffer, the delayed-immediate release minitablets exhibit substantially no release of mesalazine at pH 1.2 and pH 4.5, and release substantially all mesalazine within 90 minutes at pH 7.0.

In some embodiments, the delayed-immediate release minitablets of (a) release at least 50% w/w of their total mesalazine content in the distal ileum. In some embodiments, the delayed-immediate release minitablets of (a) release at least 70% w/w of their total mesalazine content in the distal ileum. In some embodiments, the delayed-immediate release minitablets of (a) release at least 30% w/w of their total mesalazine content in the distal ileum.

In some embodiments, the delayed-extended release minitablets release mesalazine at a pH of about 7 or greater. In some embodiments, when subject to in vitro dissolution testing according to USP Type 1 Basket at 37° C. and 100 rpm in 500 mL dissolution medium of pH 1.2 buffer for 2 hours, followed by pH 4.5 buffer for 2 hours, followed by pH 7.0 buffer for 12 hours, the delayed-extended release minitablets exhibit substantially no release of mesalazine at pH 1.2 and pH 4.5, and exhibit extended release of mesalazine over at least 4 hours at pH 7.0. In some embodiments, when subject to in vitro dissolution testing according to USP Type 1 Basket at 37° C. and 100 rpm in 500 mL dissolution medium of pH 1.2 buffer for 2 hours, followed by pH 4.5 buffer for 2 hours, followed by pH 7.0 buffer for 12 hours, the delayed-extended release minitablets exhibit substantially no release of mesalazine at pH 1.2 and pH 4.5, and exhibit extended release of mesalazine over at least 6 hours at pH 7.0. In some embodiments, when subject to in vitro dissolution testing according to USP Type 1 Basket at 37° C. and 100 rpm in 500 mL dissolution medium of pH 1.2 buffer for 2 hours, followed by pH 4.5 buffer for 2 hours, followed by pH 7.0 buffer for 12 hours, the delayed-extended release minitablets exhibit substantially no release of mesalazine at pH 1.2 and pH 4.5, and exhibit extended release of mesalazine over at least 8 hours at pH 7.0. In some embodiments, when subject to in vitro dissolution testing according to USP Type 1 Basket at 37° C. and 100 rpm in 500 mL dissolution medium of pH 1.2 buffer for 2 hours, followed by pH 4.5 buffer for 2 hours, followed by pH 7.0 buffer for 12 hours, the delayed-extended release minitablets exhibit substantially no release of mesalazine at pH 1.2 and pH 4.5, and exhibit extended release of mesalazine over at least 12 hours at pH 7.0.

In some embodiments, the delayed-extended release minitablets of (b) release at least 50% w/w of their total mesalazine content in the colon. In some embodiments, the delayed-extended release minitablets of (b) release at least 70% w/w of their total mesalazine content in the colon.

In some embodiments, the relative amounts of (a) and (b) in the unit dose pharmaceutical product are such that at least 50% w/w of the mesalazine provided in the unit dose pharmaceutical is present in the delayed-extended release minitablets (b). In some embodiments, the relative amounts of (a) and (b) in the unit dose pharmaceutical product are such that at least 60% w/w of the mesalazine provided in the unit dose pharmaceutical is present in the delayed-extended release minitablets (b). In some embodiments, the relative amounts of (a) and (b) in the unit dose pharmaceutical product are such that at least 65% w/w of the mesalazine provided in the unit dose pharmaceutical is present in the delayed-extended release minitablets (b). In some embodiments, the relative amounts of (a) and (b) in the unit dose pharmaceutical product are such that at least 70% w/w of the mesalazine provided in the unit dose pharmaceutical is present in the delayed-extended release minitablets (b). In some embodiments, the relative amounts of (a) and (b) in the unit dose pharmaceutical product are such that at least 75% w/w of the mesalazine provided in the unit dose pharmaceutical is present in the delayed-extended release minitablets (b). In some embodiments, the relative amounts of (a) and (b) in the unit dose pharmaceutical product are such that at least 80% w/w of the mesalazine provided in the unit dose pharmaceutical is present in the delayed-extended release minitablets (b). In some embodiments, the relative amounts of (a) and (b) in the unit dose pharmaceutical product are such that at least 85% w/w of the mesalazine provided in the unit dose pharmaceutical is present in the delayed-extended release minitablets (b). In some embodiments, the relative amounts of (a) and (b) in the unit dose pharmaceutical product are such that at least 90% w/w of the mesalazine provided in the unit dose pharmaceutical is present in the delayed-extended release minitablets (b).

In some embodiments, the total amount of mesalazine in the unit dose pharmaceutical product is about 0.4 g to about 6 g. In some embodiments, the total amount of mesalazine in the unit dose pharmaceutical product is about 2 g or about 4 g.

In some embodiments, the compressed matrix of (a) and the compressed matrix of (b) comprise at least 85% w/w mesalazine. In some embodiments, the compressed matrix of (a) and the compressed matrix of (b) comprise at least 90% w/w mesalazine.

In some embodiments, the compressed matrix of (a) and the compressed matrix of (b) comprise micronized mesalazine. In some embodiments, the micronized mesalazine has a particle size distribution such that the $90^{th}$ percentile, D(v, 0.9), is no more than 30 μm. In some embodiments, the micronized mesalazine has a particle size distribution such that a typical value D(v, 0.9), is about 16-17 μm.

In some embodiments, the mesalazine has a particle size distribution such that the $90^{th}$ percentile is no more than 100 μm. In some embodiments, the mesalazine has a particle size distribution such that a typical value D(v, 0.9), is about 40-50 μm.

In some embodiments, the compressed matrix of (a) and the compressed matrix of (b) comprise mesalazine and a pharmaceutically acceptable binder. In some embodiments, the compressed matrix of (a) and the compressed matrix of (b) comprise mesalazine and povidone. In some embodiments, the compressed matrix of (a) and the compressed matrix of (b) comprise mesalazine, a pharmaceutically acceptable binder, a pharmaceutically acceptable filler, and a pharmaceutically acceptable lubricant. In some embodiments, the compressed matrix of (a) and the compressed matrix of (b) comprise mesalazine, povidone, microcrystalline cellulose, and magnesium stearate. In some embodiments, the pH-dependent enteric coating of (a) comprises one or more polymers selected from the group consisting of poly[methacrylic acid-co-ethyl acrylate (1:1)] (methacrylic acid and ethyl acrylate copolymer (1:1)), hypromellose acetate succinate, and hypromellose phthalate. In some embodiments, the pH-dependent enteric coating of (b) comprises one or more polymers selected from the group consisting of poly(methyl acrylate-co-methyl methacrylate-co-methacrylic acid) [7:3:1], methacrylic acid and methyl methacrylate copolymer (1:2), and hypromellose acetate succinate. In some embodiments, the pH-independent extended release coating of (b) comprises a pH-independent extended release polymer and a pore-forming agent. In some embodiments, the pH-independent extended release coating of (b) comprises ethyl cellulose and a pore-forming agent. In some embodiments, the pH-independent extended release coating of (b) comprises ethyl cellulose and hydroxypropyl methylcellulose. In some embodiments, the minitablets of (a) and/or the minitablets of (b) further comprise a seal coat exterior to the pH-dependent enteric coating.

In some embodiments, the minitablets of (a) and the minitablets of (b) have a diameter of 1-4 mm. In some embodiments, the minitablets of (a) and the minitablets of (b) have a length of 1-4 mm.

In some embodiments, minitablets of (a) and the minitablets of (b) are provided in a sachet, capsule, or vial.

In another aspect, provided herein are methods of administering mesalazine to a subject in need thereof, or for treating inflammatory bowel disease, such as ulcerative colitis and mild-to-moderate Crohn's disease, comprising orally administering to the subject a unit dose pharmaceutical product as described herein.

In another aspect, provided herein are uses of mesalazine in the preparation of a medicament for orally administering mesalaizine to a subject in need thereof, or for treating inflammatory bowel disease, such as ulcerative colitis and mild-to-moderate Crohn's disease, wherein the medicament comprises a unit dose pharmaceutical product as described herein.

In another aspect, provided herein are unit dose pharmaceutical products as described herein for orally administering mesalazine to a subject in need thereof, or for treating inflammatory bowel disease, such as ulcerative colitis and mild-to-moderate Crohn's disease.

DETAILED DESCRIPTION

Described herein are pharmaceutical compositions for the oral administration of mesalazine, methods of making such pharmaceutical compositions, and therapeutic methods for using them. In accordance with some embodiments, the compositions deliver mesalazine to the lower gastrointestinal tract, such as the distal ileum and/or the colon, over a period of time sufficient to achieve therapeutic effect. In accordance with some embodiments, there are provided compositions comprising (a) a plurality of delayed-immediate release minitablets comprising mesalazine that selectively release mesalazine in the distal ileum and (b) a plurality of delayed-extended release minitablets comprising mesalazine that selectively release mesalazine in the colon. In some embodiments, the compositions are provided in the form of unit dose pharmaceutical products comprising (a) a plurality of delayed-immediate release minitablets comprising mesalazine that selectively release mesalazine in the distal ileum and (b) a plurality of delayed-extended release minitablets comprising mesalazine that selectively release mesalazine in the colon.

Definitions

Technical and scientific terms used herein have the meanings commonly understood by one of ordinary skill in the art of pharmaceutical formulations to which the present disclosure pertains, unless otherwise defined. Reference is made herein to various methodologies known to those of ordinary skill in the art. Suitable materials and/or methods known to those of ordinary skill in the art can be utilized in carrying out the present disclosure. However, specific materials and methods are described. Materials, reagents and the like to which reference is made in the following description and examples are obtainable from commercial sources, unless otherwise noted.

As used herein, the singular forms "a," "an," and "the" designate both the singular and the plural, unless expressly stated to designate the singular only.

As used herein, the term "about" means that the number or range is not limited to the exact number or range set forth, but encompass values around the recited number or range as will be understood by persons of ordinary skill in the art depending on the context in which the number or range is used. Unless otherwise apparent from the context or convention in the art, "about" means up to plus or minus 10% of the particular term.

As used herein, "subject" denotes any mammal, including humans. For example, a subject may be suffering from or at risk of developing a condition that can be diagnosed, treated or prevented with mesalazine, or may be taking mesalazine for other purposes.

The terms "administer," "administration," or "administering" as used herein refer to (1) providing, giving, dosing and/or prescribing, such as by either a health professional or his or her authorized agent or under his direction, and (2) putting into, taking or consuming, such as by a health professional or the subject.

The terms "treat", "treating" or "treatment", as used herein, include alleviating, abating or ameliorating a disease or condition or one or more symptoms thereof, whether or not the disease or condition is considered to be "cured" or "healed" and whether or not all symptoms are resolved. The terms also include reducing or preventing progression of a disease or condition or one or more symptoms thereof, impeding or preventing an underlying mechanism of a disease or condition or one or more symptoms thereof, and achieving any therapeutic and/or prophylactic benefit.

As used herein, the phrase "therapeutically effective amount" refers to a dose that provides the specific pharmacological effect for which the drug is administered in a subject in need of such treatment. It is emphasized that a therapeutically effective amount will not always be effective in treating the conditions described herein, even though such dose is deemed to be a therapeutically effective amount by those of skill in the art. For convenience only, exemplary doses and therapeutically effective amounts are provided below with reference to adult human subjects. Those skilled in the art can adjust such amounts in accordance with standard practices as needed to treat a specific subject and/or condition/disease.

As used herein, a composition that "selectively releases" an active agent (e.g. mesalazine) in a specific region of the digestive tract (e.g., the distal ileum or colon) refers to a composition that, after oral administration, releases most of its active agent in that region, such as by not releasing more than 25%, w/w more than 30% w/w, more than about 40% w/w, or more than about 50% w/w of the total amount of active agent until the composition reaches that specific region of the digestive tract, and/or by releasing more than about 50% w/w, more than about 60% w/w, more than about 70% w/w or more than about 75% w/w of the total amount of active agent in the composition in that region of the digestive tract. A composition that "selectively releases" an active agent in a specific region of the digestive tract may exhibit release of active agent higher (earlier) in the digestive tract, lower (later) in the digestive tract, or both.

As used herein, the term "mesalazine" includes mesalazine (also known as "mesalamine") and pharmaceutically acceptable salts and esters thereof. In contrast, the terms "5-aminosalicylic acid" and "5-ASA" are used to refer to mesalazine specifically, as distinguished from pharmaceutically acceptable salts and esters thereof.

As used herein, the term "minitablets" refers to a solid form prepared by compression of the active ingredient (e.g., mesalazine) with one or more pharmaceutically acceptable excipients (including but not limited to, fillers, binders, lubricants, and the like), typically by using a tableting machine (such as a rotary tablet press) that produces smooth tablets of uniform shape and size. Minitablets typically have a size ranging from about 1 mm to about 3 mm in diameter, and optionally may be provided with one or more pharmaceutically acceptable coatings.

Mesalazine

As noted above, the compositions described herein include mesalazine (or a pharmaceutically acceptable salt or ester thereof). Mesalazine is also known as 5-aminosalicylic acid, 2-hydroxy 5-aminobenzoic acid, 3-carboxy-4-hydroxyaniline, mesalamine, and 5-amino-2-hydroxybenzoic acid, and has the molecular formula $C_7H_7NO_3$ and a molecular weight of 153.14. It is registered under CAS Registry Number 89-57-6 and Einecs 201-919-1.

Exemplary pharmaceutically acceptable salts include acid addition salts, such as hydrochloride salts. Any pharmaceutically acceptable salt can be used, such as sodium and calcium salts. Other non-limiting exemplary salts include salts formed with a carboxylic acid group, alkali metal salts, and alkaline earth metal salts. Non-limiting examples of pharmaceutically acceptable esters include straight chain or branched $C_1$-$C_{18}$ alkyl esters, including methyl, ethyl, propyl, isopropyl, butyl, isobutyl, amyl, hexyl, heptyl, octyl, nonyl, decyl, lauryl, myristyl, cetyl, and stearyl, and the like; straight chain or branched $C_2$-$C_{18}$ alkenyl esters, including vinyl, allyl, undecenyl, oleyl, linolenyl, and the like; $C_3$-$C_8$ cycloalkyl esters, including cyclopropyl, cyclobutyl, cyclopentyl, cyclohexyl, cycloheptyl and cyclooctyl, and the like; aryl esters, including phenyl, toluoyl, xylyl, naphthyl, and the like; alicyclic esters, including menthyl and the like; or aralkyl esters, including benzyl, phenethyl, and the like.

The compositions and unit dose pharmaceutical products described herein may include a therapeutically effective amount of mesalazine. The therapeutically effective amount may depend on the subject being treated, the condition being treated, the desired effect, and the intended duration of therapeutic effect of the compositions and products. A therapeutically effective amount of orally administered mesalazine for the treatment of inflammatory bowel disease, is generally about 2 to about 6 g/day for an adult human subject, optionally administered in divided two to four doses (e.g., about 4 g once a day, about 2 g two times a day, about 1 g four times a day, etc.). For example, therapeutic doses of mesalazine for patients with active ulcerative colitis of any disease extent beyond proctitis is typically from about 2 to about 5 g a day, including from about 2.4 to about 4.8 g/day, with or without concomitant rectal therapy. Thus, a unit dose pharmaceutical product as described herein may include from about 0.4 g to about 6 g mesalazine per unit dose, including about 0.4 g, 0.5 g, about 1 g, about 1.2 g, about 2 g, about 2.4 g, about 3 g, about 3.6 g, about 4 g, about 4.8 g, about 5 g, or about 6 g, such as 0.5 g, 1 g, 2 g, 3 g, 4 g, 5 g, or 6 g, and amounts between any of these values.

Compositions

As noted above, in accordance with some embodiments, there are provided compositions comprising (a) a plurality of delayed-immediate release minitablets comprising mesalazine that selectively release mesalazine in the distal ileum and (b) a plurality of delayed-extended release minitablets comprising mesalazine that selectively release mesalazine in the colon. The minitablets described herein are compressed tablets provided with one or more coatings to achieve the desired drug delivery profile.

Minitablets: The Minitablets Matrix

The compressed minitablets of the compositions described herein can have any shape, such as being spherical, substantially spherical, round, substantially round, oval, oblong, polygonal, etc. The compressed minitablets may have a longest diameter in any dimension of from about 1 mm to about 4 mm, including about 2 mm, such as having a longest diameter of 1 mm, 2 mm, 3 mm, or 4 mm. In some embodiments, the compressed minitablets have a longest diameter of about 1 mm, about 2 mm, about 3 mm, or about 4 mm, including a longest diameter of 1 mm, 2 mm, 3 mm, or 4 mm in any one dimension.

In some embodiments, the minitablets are comprised of a compressed matrix (generally excluding any coating) comprising mesalazine and one or more pharmaceutically acceptable excipients, such as fillers, binders, lubricants, and the like, as discussed in more detail below.

In some embodiments, the matrix comprises micronized mesalazine. In some embodiments, the micronized mesalazine has a particle size distribution such that the 90th percentile is no more than 30 μm (e.g., D(v, 0.9) is 30 μm). In some embodiments, the micronized mesalazine has a particle size distribution such that a typical value of D(v, 0.9) is about 16-17 μm.

In other embodiments, the matrix comprises mesalazine having D(v, 0.9) of no more than 100 μm, such as mesalazine having a typical value of D(v, 0.9) of about 40-50 μm.

The uncoated matrix of the minitablets may comprise at least 85% w/w mesalazine or more, such as at least 85% w/w, at least 86% w/w, at least 87% w/w, at least 88% w/w, at least 89% w/w, at least 90% w/w, at least 91% w/w, at least 92% w/w, at least 93% w/w, at least 94% w/w, at least 95% w/w, at least 96% w/w at least 97% w/w at least 98% w/w or at least 99% w/w mesalazine, such as about 85-98% w/w, about 86-98% w/w, about 87-98% w/w, about 88-98% w/w, about 89-98% w/w, or about 90-98% w/w. In some embodiments, the uncoated minitablets comprise about 88-98% w/w mesalazine, including about 88% w/w, 89% w/w, or 90% w/w mesalazine.

The matrix of the minitablets may comprise amounts of the one or more pharmaceutically acceptable excipients sufficient to achieve the intended effect of the excipient(s). A suitable amount of a given pharmaceutically acceptable excipient can be determined by a person of ordinary skill in the art.

As noted above, the matrix of the minitablets may comprise one or more pharmaceutically acceptable excipients, such as fillers, binders, lubricants, and the like.

Non-limiting examples of fillers include one or more of sucrose, glucose, lactose, mannitol, xylitol, dextrose, microcrystalline cellulose, co-processed microcrystalline celluloses (such as Avicel® CL-611, Avicel® RC-581, Avicel® RC-591, Avicel® CE, Avicel® DG, Avicel® HFE, Avicel® PH-102, Avicel® HFE-102, Avicel® PH-200, and Avicel® PH-302), sugars (such as sucrose, glucose, amylose, maltodextrin, dextrose and the like), maltose, sorbitol, calcium phosphate, calcium sulphate, magnesium aluminium silicate and the like. In some embodiments, the pharmaceutically acceptable filler comprises microcrystalline cellulose.

Non-limiting examples of suitable binders include one or more celluloses, such as modified celluloses (such as low substituted hydroxypropyl cellulose, hydroxypropyl cellulose (HPC), hydroxypropyl methylcellulose (HPMC, Hypromellose), hydroxyethylcellulose, hydroxyethyl methylcellulose, and ethyl cellulose), cellulose gum, xanthan gum, carrageenan, chitosan, pectinic acid, sodium alginate, starches such as corn or potato starch partially pregelatinized starches (such as Starch 1500®), polyvinyl acetate (Kollicoat® SR), polyvinyl alcohol-polyethylene glycol graft copolymer (Kollicoat® IR), vinylpyrrolidone-vinyl acetate copolymer (copovidone), acrylic acid polymers (Carbopol®), poloxamers, polycarbophil, polyethylene oxide, polyethylene glycol, polyvinylpyrrolidone (polyvinylpyrrolidone, PVP), and the like. In some embodiments, the pharmaceutically acceptable binder comprises povidone.

Non-limiting examples of lubricants include one or more of calcium stearate, glyceryl monostearate, glyceryl palmitostearate, magnesium stearate, sodium stearyl fumarate, talc powder, colloidal silicon dioxide. In some embodiments, the pharmaceutically acceptable lubricant comprises magnesium stearate.

Non-limiting examples of disintegrants include one or more of starches such as corn or potato starch, modified starches (such as sodium starch glycolate) and partially pregelatinized starches (such as Starch 1500); crosslinked polyvinylpyrrolidone (crospovidone)), crosslinked carboxymethylcellulose sodium (croscarmellose sodium), ion exchange resins (such as Polacrilin potassium, Polacrilex) Neusilins, and low substituted hydroxypropyl cellulose.

In some embodiments, the matrix of the delayed-immediate release minitablets is the same as the matrix of the delayed-extended release minitablets, e.g., the uncoated minitablets are the same. In other embodiments, the matrix of the delayed-immediate release minitablets is different from the matrix of the delayed-extended release minitablets, e.g., the uncoated minitablets are different.

In some embodiments, the matrix of the delayed-immediate release minitablets comprises mesalazine and one or more of a pharmaceutically acceptable binder, a pharmaceutically acceptable filler, and a pharmaceutically acceptable lubricant. In some embodiments, the matrix of the delayed-immediate release minitablets comprises mesalazine and povidone. In some embodiments, the matrix of the delayed-immediate release minitablets comprises mesalazine, povidone, microcrystalline cellulose, and magnesium stearate.

In some embodiments, the matrix of the delayed-extended release minitablets comprises mesalazine and one or more of a pharmaceutically acceptable binder, a pharmaceutically acceptable filler, and a pharmaceutically acceptable lubricant. In some embodiments, the matrix of the delayed-extended release minitablets comprises mesalazine and povidone. In some embodiments, the matrix of the delayed-extended release minitablets comprises mesalazine, povidone, microcrystalline cellulose, and magnesium stearate.

Minitablets: The Minitablets Coatings

As noted above, in accordance with some embodiments, the compositions described herein may comprise a plurality of delayed-immediate release minitablets comprising mesalazine that selectively release mesalazine in the distal ileum. In some embodiments, delayed-immediate release is achieved by providing minitablets as described herein with a delayed release coating that delays release of mesalazine from the minitablets substantially until the minitablets reach the distal ileum, to achieve selective release in the distal ileum. In some embodiments, the delayed release coating is a pH-dependent enteric coating that achieves release of mesalazine at a pH of greater than or equal to about 5.5.

As also noted above, in accordance with some embodiments, the compositions described herein may comprise a plurality of delayed-extended release minitablets comprising mesalazine that selectively release mesalazine in the colon. In some embodiments, delayed-extended release is achieved by providing minitablets as described herein with an inner extended release coating and an outer delayed release coating that delays release of mesalazine from the minitablets substantially until the minitablets reach the colon, to achieve selective release in the colon. In some embodiments, the inner extended release coating is a pH-independent extended release coating and the outer delayed release coating is a pH-dependent enteric coating that achieves release of mesalazine at a pH of greater than or equal to about 7.

pH-Dependent Enteric Coatings

As noted above, in some embodiments the compositions comprise minitablets provided with a delayed release coating. In some embodiments, the delayed release coating is a pH-dependent enteric coating. In some embodiments, the delayed-immediate release minitablets are provided with a pH-dependent enteric coating that achieves mesalazine release at a pH of about 5.5 or greater. In some embodiments, the delayed-extended release minitablets are provide with a pH-dependent enteric coating that achieves mesalazine release at a pH of about 7 or greater.

pH-dependent enteric coatings that achieve release at specific pH values are known in the art, and typically comprise polymers with a solubility in the aqueous environment of the gastrointestinal tract that is pH-dependent (referred to as "enteric polymers"). Typical polymers used for this purpose include methacrylic acid copolymers, polysorbate polymers, cellulose acetate phthalate, hydroxypropyl methylcellulose phthalate, hydroxypropyl methylcellulose acetate succinate, polyvinyl acetate phthalate, cellulose acetate trimellitate, carboxymethylethylcellulose, and shellac. Commercially available enteric polymers include those sold by Evonik Industries under the Eudragit® trademark, including Eudragit® L (methacrylic acid and methyl methacrylate copolymer 1:1), and Eudragit® S (methacrylic acid and methyl methacrylate copolymer 1:2). For example, Eudragit® L 30 D-55 (methacrylic acid and ethyl acrylate copolymer 1:1 dispersion) and Eudragit® L-100-55 (methacrylic acid and ethyl acrylate copolymer 1:1) are reported to dissolve above pH 5.5, Eudragit® L 100 (methacrylic acid and methyl methacrylate copolymer 1:1) and Eudragit® L 12.5 (methacrylic acid and methyl methacrylate copolymer 1:1 solution) are reported to dissolve above pH 6.0, and Eudragit® S 100 (methacrylic acid and methyl methacrylate copolymer 1:2), Eudragit® S 12.5 (methacrylic acid and methyl methacrylate copolymer 1:2 dispersion) and Eudragit® FS 30D (poly(methyl acrylate-co-methyl methacrylate-co-methacrylic acid) 7:3:1 dispersion) are reported to dissolve above pH 7.0. Another commercially available enteric polymer is sold by ShinEtsu as AQOAT® (hypromellose acetate succinate).

pH-dependent enteric coatings may include a single enteric polymer or a mixture of enteric polymers. The relative amounts of the enteric polymers in the delayed release coating and the thickness at which the coating is applied to the minitablets can be independently selected to achieve release at the intended pH, e.g., at the intended site of the gastrointestinal tract. For example, the polymer(s) can be selected and combined in relative amounts and applied at a thickness to achieve dissolution at the target pH, e.g., at a pH of about 5.5 or a pH of about 7 or greater.

In some embodiments, the pH-dependent enteric coating of the delayed-immediate release minitablets comprises one or more of methacrylic acid and ethyl acrylate copolymer (1:1) (e.g., Eudragit® L 30D-55), hypromellose acetate succinate, and hypromellose phthalate. In some embodiments, the pH-dependent enteric coating of the delayed-extended release minitablets comprises one or more of poly(methyl acrylate-co-methyl methacrylate-co-methacrylic acid) [7:3:1] and hypromellose acetate succinate. In some embodiments, the pH-dependent enteric coating of the delayed-extended release minitablets comprises methacrylic acid and methyl methacrylate copolymer 1:2 (e.g., Eudragit® S 100). In some embodiments, the pH-dependent enteric coating of the delayed-extended release minitablets comprises poly(methyl acrylate-co-methyl methacrylate-co-methacrylic acid) [7:3:1] and triethyl citrate (e.g., PlasACRYL™ T20). In some embodiments, the pH-dependent enteric coating of the delayed-extended release minitablets comprises methacrylic acid and methyl methacrylate copolymer 1:2 (e.g., Eudragit® S 100) and triethyl citrate (e.g., PlasACRYL™ T20).

pH-Independent Extended Release Coatings

As noted above, in some embodiments the compositions comprise minitablets provided with an extended release coating. In some embodiments, the extended release coating is a pH-independent extended release coating.

pH-independent extended release coatings are known in the art, and may comprise an extended release polymer and a pore-forming agent.

Extended release polymers suitable for this purpose are known in the art and include hydrophobic polymers with solubility profiles that are substantially flat over a pH range of 1-9. Pore-forming agents suitable for this purpose are known in the art, and include agents that dissolve in an aqueous environment, leaving pores in the coating, thereby allowing release of the active agent through the pores.

Typical extended release polymers used for this purpose include hydrophobic polymers such as cellulose ethers. Non-limiting examples of suitable cellulose ethers include ethyl cellulose, cellulose acetate and the like; polyvinyl esters such as polyvinyl acetate, polyacrylic acid esters, methacrylic and acrylate polymers (pH-independent types); high molecular weight polyvinyl alcohols and waxes such as fatty acids and glycerides, methacrylic acid ester neutral polymers, polyvinyl alcohol-maleicanhydride copolymers and the like; ethylacrylate-methylmethacrylate copolymers; aminoalkyl methacrylate copolymers; and mixtures thereof. In some embodiments the pH-independent extended release coating includes ethyl cellulose.

Typical pore-forming agents used for this purpose include copovidone; water soluble polymers such as polyvinylpyrrolidone (PVP); water-soluble cellulose derived materials, such as hydroxyethyl cellulose, hydroxypropyl methylcellulose, hydroxypropyl cellulose (also referred to as hypromellose); inorganic salts; sugars; hydroxylated compounds, including polyvinyl alcohols and glycols, such as polyethylene glycol and propylene glycol; pH-dependent pore formers, such as methacrylic acid copolymers such as Eudragit® L (methacrylic acid and methyl methacrylate copolymer 1:1), Eudragit® S (methacrylic acid and methyl methacrylate copolymer 1:2), Eudragit® FS 30D (poly (methyl acrylate-co-methyl methacrylate-co-methacrylic acid) 7:3:1), Eudragit® L30D-55 (methacrylic acid and ethyl acrylate copolymer 1:1 dispersion) and Eudragit® L100-55 (methacrylic acid and ethyl acrylate copolymer 1:1); alginic acid and alginate salts and the like; disintegrants; and mixtures of any two or more thereof. In some embodiments the pH-independent extended release coating includes hydroxypropyl methylcellulose (hypromellose) as a pore-forming agent.

Non-limiting examples of disintegrants include one or more of starches such as corn or potato starch, modified starches (such as sodium starch glycolate) and partially pregelatinized starches (such as Starch 1500); crosslinked polyvinylpyrrolidone (crospovidone), crosslinked carboxymethylcellulose sodium (croscarmellose sodium), ion exchange resins (such as Polacrilin potassium, Polacrilex) Neusilins, and low substituted hydroxypropyl cellulose. In some embodiments, disintegrants can be used as pore-forming agents.

Alternatively, a pH-independent extended release coatings may comprise a waxy material and a hydrophilic polymer. Typical waxy materials used for this purpose include hydrophobic waxy materials, such as one or more of carnauba wax, white wax, candelilla wax, beeswax, cetylester wax, montan wax, microcrystalline wax, lecithin, hydrogenated tallow, paraffin wax, sellac wax, paraffin soft, glyceryl behenate, glyceryl palmitoesterarate, glyceryl diestearate, tribehenin, glycerol esters such as glyceryl behenate and glyceryl palmitostearate, fatty alcohols (particularly those having 12-24 carbon atoms, such as cetyl alcohol, cetostearyl alcohol, lauryl alcohol, myristyl alcohol, stearyl alcohol, palmityl alcohol, etc.), fatty acids (particularly those having 12-24 carbon atoms, such as lauric acid, myristic acid, stearic acid, palmitic acid, etc.), castor wax (i.e., hydrogenated castor-oil), $C_{16-30}$ fatty acid triglycerides, stearyl polyoxil-32 glyceride, behenoyl polyoxil-8 glyceride, lauroyl polyoxil glycerides, and steral polyoxil glycerides. For example, the waxy material may comprise one or more of white wax, glyceryl behenate, glyceryl palmitoesterarate and fatty alcohols such as cetyl alcohol, cetostearyl alcohol, lauryl alcohol, myristyl alcohol, stearyl alcohol and palmityl alcohol.

Typical hydrophilic polymers used for this purpose include one or more of polyvinyl alcohol, sodium carboxy methylcellulose, hydroxypropylcellulose, hydroxypropylmethyl cellulose, hydroxyethylmethylcellulose, polyvinylpyrrolidone, copovidone starch or its derivatives, sodium alginate, calcium alginate, sodium carboxymethylcellulose, calcium carboxymethylcellulose, polyethylene glycol (PEG) having a molecular weight of greater than 1000 number average molecular weight (e.g., PEG 3350, PEG 4600, PEG 6000, PEG 8000, PEG 12000 and PEG 20000), polyethylene oxide, and enteric polymers.

In some embodiments, the extended release coating comprises ethyl cellulose and a pore-forming agent, such as hydroxypropyl methylcellulose.

The relative amounts of extended release polymer and pore-forming agent (or waxy substance and hydrophilic polymer) in the extended release coating and the thickness at which the coating is applied to the minitablets can be independently selected to achieve the desired extended release profile. For example, increasing the relative amount of pore-forming agent generally will increase the release rate, and increasing the thickness of the coating on the minitablets generally will decrease the release rate. Exemplary extended release coating coating weights are illustrated in the examples, and include coating weights of from about 2% to about 15%. In some embodiments, an extended release coating is applied to a mesalazine minitablet at a coating weight of from about 3% to about 10%.

Any coating as described herein also may include a lubricant and/or a plasticizer. Typical lubricants used for this purpose include one or more of calcium stearate, glyceryl monostearate, glyceryl palmitostearate, magnesium stearate, sodium stearyl fumarate, and sodium lauryl sulfate. In some embodiments, a coating includes a lubricant. Typical plasticizers used for this purpose include one or more of glycerin, polyethylene glycols, polyethylene glycol monomethyl ether, propylene glycol, sorbitol sorbitan solution, acetyl tributyl citrate, acetyl triethyl citrate, castor oil, diacetylated monoglycerides, dibutyl sebacate, diethyl phthalate, triacetin, tributyl citrate, triethyl citrate, glyceryl monostearate, glyceryl palmitostearate, and sodium stearyl fumarate. In some embodiments, a coating includes a plasticizer, such as dibutyl sebacate or triethyl citrate.

Any coating as described herein also may include other components, such as an anti-tack agent such as talc, and/or colloidal silicon dioxide, calcium stearate, magnesium stearate, and combinations of any two or more thereof. In some embodiments, a coating includes talc.

Any coating as described herein also may include a surfactant. Typical surfactants used for this purpose include one or more of sodium dodecylsulfate, polysorbate 80, polysorbate 20, polysorbate 40, polysorbate 60, polysorbate 65, polysorbate 85, polysorbate 80, polysorbate 21, polysorbate 61, poloxamer 188, and macrogolglycerol ricinoleate.

Delayed-Immediate Release Tablets

As noted above, the delayed-immediate release minitablets (DR/IR minitablets) described herein comprise a compressed matrix comprising mesalazine as described above provided with a pH-dependent enteric coating as described above. In some embodiments, the delayed-immediate release minitablets selectively release mesalazine in the distal ileum. In some embodiments, the delayed-immediate release minitablets release mesalazine at a pH of about 5.5. or greater. In some embodiments, the delayed-immediate release minitablets selectively release mesalazine in the distal ileum, and may continue to release mesalazine lower/later in the digestive tract. In some embodiments, the delayed-immediate release minitablets do not release more than 25% w/w, more than 30% w/w, more than about 40% w/w, or more than about 50% w/w of the total amount of mesalazine until the minitablets reach the distal ileum, and/or release at least about 50% w/w of their total mesalazine content in the distal ileum, such as at least 50% w/w/, about 50% w/w, at least 60% w/w/, about 60% w/w, at least 70% w/w/, about 70% w/w, at least 75% w/w/, about 75% w/w, or greater, in the distal ileum.

In some embodiments, when subject to in vitro dissolution testing according to USP Type 1 Basket at 37° C. and 100 rpm in 500 mL dissolution medium of pH 1.2 buffer for 2 hours, followed by pH 4.5 buffer for 2 hours, followed by pH 6.8 buffer for 2 hours, delayed-immediate release minitablet described herein exhibit substantially no release of mesalazine at pH 1.2 and pH 4.5, and release substantially all mesalazine within 120 minutes at pH 6.8.

In some embodiments, when subject to in vitro dissolution testing according to USP Type 1 Basket at 37° C. and 100 rpm in 500 mL dissolution medium of pH 1.2 buffer for 2 hours, followed by pH 4.5 buffer for 2 hours, followed by pH 7.0 buffer, delayed-immediate release minitablet described herein exhibit substantially no release of mesalazine at pH 1.2 and pH 4.5, and release substantially all mesalazine within 120 minutes at pH 7.0.

In some embodiments, when subject to in vitro dissolution testing according to USP Type 1 Basket at 37° C. and 100 rpm in 500 mL dissolution medium of pH 1.2 buffer for 2 hours, followed by pH 4.5 buffer for 2 hours, followed by pH 6.8 buffer for 2 hours, delayed-immediate release minitablets described herein exhibit substantially no release of mesalazine at pH 1.2 and pH 4.5, and release substantially all mesalazine within 90 minutes at pH 6.8.

In some embodiments, when subject to in vitro dissolution testing according to USP Type 1 Basket at 37° C. and 100 rpm in 500 mL dissolution medium of pH 1.2 buffer for 2 hours, followed by pH 4.5 buffer for 2 hours, followed by pH 7.0 buffer, delayed-immediate release minitablets described herein exhibit substantially no release of mesalazine at pH 1.2 and pH 4.5, and release substantially all mesalazine within 90 minutes at pH 7.0.

The delayed-immediate release of mesalazine at a pH of about 5.5 or above achieved by the DR/IR minitablets achieves targeted delivery and selective release of mesalazine to the distal ileum, thus providing mesalazine to the distal ileum where it can exert therapeutic effect.

Delayed-Extended Release Tablets

As noted above, the delayed-extended release minitablets (DR/ER minitablets) described herein comprise a compressed matrix comprising mesalazine as described above provided with an inner pH-independent extended release coating as described above and an outer pH-dependent enteric coating as described above. In some embodiments, the delayed-extended release minitablets selectively release mesalazine in the colon. In some embodiments, the delayed-extended release minitablets described herein release mesalazine at a pH of about 7 or above. In some embodiments, the delayed-extended release minitablets do not release more than 25%, w/w more than 30% w/w, more than about 40% w/w, or more than about 50% w/w of the total amount of mesalazine until the minitablets reach the colon, and/or release at least about 50% w/w of their total mesalazine content in the colon, such as at least 50% w/w/, about 50% w/w, at least 60% w/w/, about 60% w/w, at least 70% w/w/, about 70% w/w, at least 75% w/w/, about 75% w/w, or greater, in the colon.

In some embodiments, when subject to in vitro dissolution testing according to USP Type 1 Basket at 37° C. and 100 rpm in 500 mL dissolution medium of pH 1.2 buffer for 2 hours, followed by pH 4.5 buffer for 2 hours, followed by pH 7.0 buffer for 12 hours, delayed-extended release minitablets described herein exhibit substantially no release of mesalazine at pH 1.2 and pH 4.5, and exhibit extended release of mesalazine over at least 4 hours at pH 7.0. In some embodiments, delayed-extended release tablets may exhibit at least 90% release of mesalazine within 12 hours, within 18 hours, within 24 hours, within 36 hours, or within 48 hours at pH 7.0 or greater.

In some embodiments, when subject to in vitro dissolution testing according to USP Type 1 Basket at 37° C. and 100 rpm in 500 mL dissolution medium of pH 1.2 buffer for 2 hours, followed by pH 4.5 buffer for 2 hours, followed by pH 7.0 buffer for 12 hours, delayed-extended release minitablets exhibit substantially no release of mesalazine at pH 1.2 and pH 4.5, and exhibit extended release of mesalazine over at least 6 hours, over at least 8 hours, or over at least 12 hours at pH 7.0. In some embodiments, delayed-extended release tablets may exhibit at least 90% release of mesalazine over within 12 hours, within 18 hours, within 24 hours, within 36 hours, or within 48 hours at pH 7.0 or greater.

The delayed-extended release of mesalazine achieved by the DR/ER minitablets achieves targeted delivery and selective, extended release of mesalazine in the colon, thus providing mesalazine to the colon where it can exert therapeutic effect.

Other Coatings

In some embodiments, one or both of the delayed-immediate release minitablets described herein and the delayed-extended release minitablets described herein may further comprise an additional pharmaceutically acceptable coating. In some embodiments, one or both types of minitablets are provided with a seal coat exterior to the pH-dependent enteric coating and/or a colored coating exterior to the pH-dependent enteric coating.

Unit Dose Pharmaceutical Products

As noted above, also provided herein are unit dose pharmaceutical products comprising (a) a plurality of delayed-immediate release minitablets as described herein that selectively release mesalazine in the distal ileum and (b) a plurality of delayed-extended release minitablets as described herein that selectively release mesalazine in the colon.

A unit dose pharmaceutical product as described herein comprises a unit dose of mesalazine, which may be a therapeutically effective amount of mesalazine, including a therapeutically effective daily dose of mesalazine or a divided dose of a therapeutically effective daily dose of mesalazine. As discussed above, a therapeutically effective amount of mesalazine for the treatment of inflammatory bowel disease, such as ulcerative colitis and mild-to-moderate Crohn's disease, is generally about 2 to about 6 g per day for an adult human subject, optionally administered in two to four divided doses (e.g., about 4 g once a day, about 2 g two times a day, about 1 g four times a day, etc.). For example, therapeutic doses of mesalamine for patients with active ulcerative colitis of any disease extent beyond proctitis is typically from about 2 to about 5 g a day, including from about 2.4 to about 4.8 g/day, with or without concomitant rectal therapy. Thus, a unit dose pharmaceutical product as described herein may include from about 0.4 g to about 6 g mesalazine per unit dose, including about 0.4 g, 0.5 g, about 1 g, about 1.2 g, about 2 g, about 2.4 g, about 3 g, about 3.6 g, about 4 g, about 4.8 g, about 5 g, or about 6 g, such as 0.5 g, 1 g, 2 g, 3 g, 4 g, 5 g, or 6 g, and amounts between any of these values.

A unit dose pharmaceutical product as described herein may be formulated to deliver one amount of mesalazine to the distal ileum and to deliver a second amount of mesalazine to the colon, by providing a first selected amount of mesalazine in the delayed-immediate release (DR/IR) minitablets and a second selected amount of mesalazine in the delayed-extended release (DR/ER) minitablets. The amounts of mesalazine provided in each type of minitablet may be selected based on the specific disease or condition being treated, such as the nature and extent of the disease state in various regions of the digestive tract, such as the distal ileum and/or colon. Thus, from about 10 to about 90% w/w of the mesalazine provided in a unit dose pharmaceutical product may be present in the delayed-immediate release (DR/IR) minitablets, and from about 90 to about 10% w/w of the mesalazine may be present in the delayed-extended release (DRIER) minitablets. For example at least 50% w/w, such as about 50% w/w, or at least 70% w/w, such as about 70% w/w, about 75% w/w, about 80% w/w, or greater, of the mesalazine provided in a unit dose pharmaceutical product may be present in the delayed-extended release (DRIER) minitablets, based on the total weight of the mesalazine provided in the delayed-immediate release minitablets and the delayed-extended release minitablets. In some embodiments, about 50 w/w of the mesalazine provided in the unit dose pharmaceutical product is provided in the DR/IR minitablets and about 50% w/w of the mesalazine is provided in the DR/ER minitablets. In other embodiments, at least about 50% w/w, at least about 60% w/w, at least about 70% w/w, at least about 75% w/w, or at least about 80% w/w of the mesalazine is provided in the DR/ER minitablets, such as 50% w/w, from 50-80% w/w, about 60% w/w, about 65% w/w, about 70% w/w, about 70% w/w, about 75% w/w, about 75% w/w, about 80% w/w, about 85% w/w, and about 90% w/w of the mesalazine being provided in the DR/ER minitablets.

In some embodiments, when subject to in vitro dissolution testing according to USP Apparatus 2 at 37° C. and 100 rpm in 750 mL of 0.1N HCL for 2 hours, followed by 1000 mL of pH 7 phosphate buffer for 12 hours, a unit dose pharmaceutical product as described herein exhibits release of mesalazine of ≤10% at 2 hours, 45-75% at 6 hours, and ≥90% at 14 hours.

In some embodiments, a unit dose pharmaceutical product is in the form of a sachet, capsule or vial containing a unit dose of the DR/IR and DR/ER minitablets.

Methods of Manufacture

The compositions described herein can be made by methods known in art. In general the minitablet matrices are manufactured by wet granulation, roller compaction or direct compression processes. In some embodiments, the DR/IR minitablets are made by coating minitablet matrices with a pH-dependent enteric coating. In some embodiments, the DR/ER minitablets are made by coating minitablet matrices with a pH-independent extended release coating and a pH-dependent enteric coating, with appropriate drying times between coatings. Unit dose pharmaceutical products are prepared by filling a container (e.g., a sachet, capsule or vial) with a unit dose of the DR/IR and DR/ER minitablets.

In some embodiments, the minitablet matrices have a hardness of about 1.0-3.0 kp, including a hardness of about 1.0, about 2.0, or about 3.0 kp. In some embodiments, the minitablet matrices have a friability of no more than about 1.0%. In some embodiments, the minitablet matrices have a friability of no more than about 0.7%. In some embodiments, the minitablet matrices have a friability of no more than about 0.5%. In accordance with these embodiments, the minitablets are stronger than the granules used in current mesalazine products.

Figure 1:
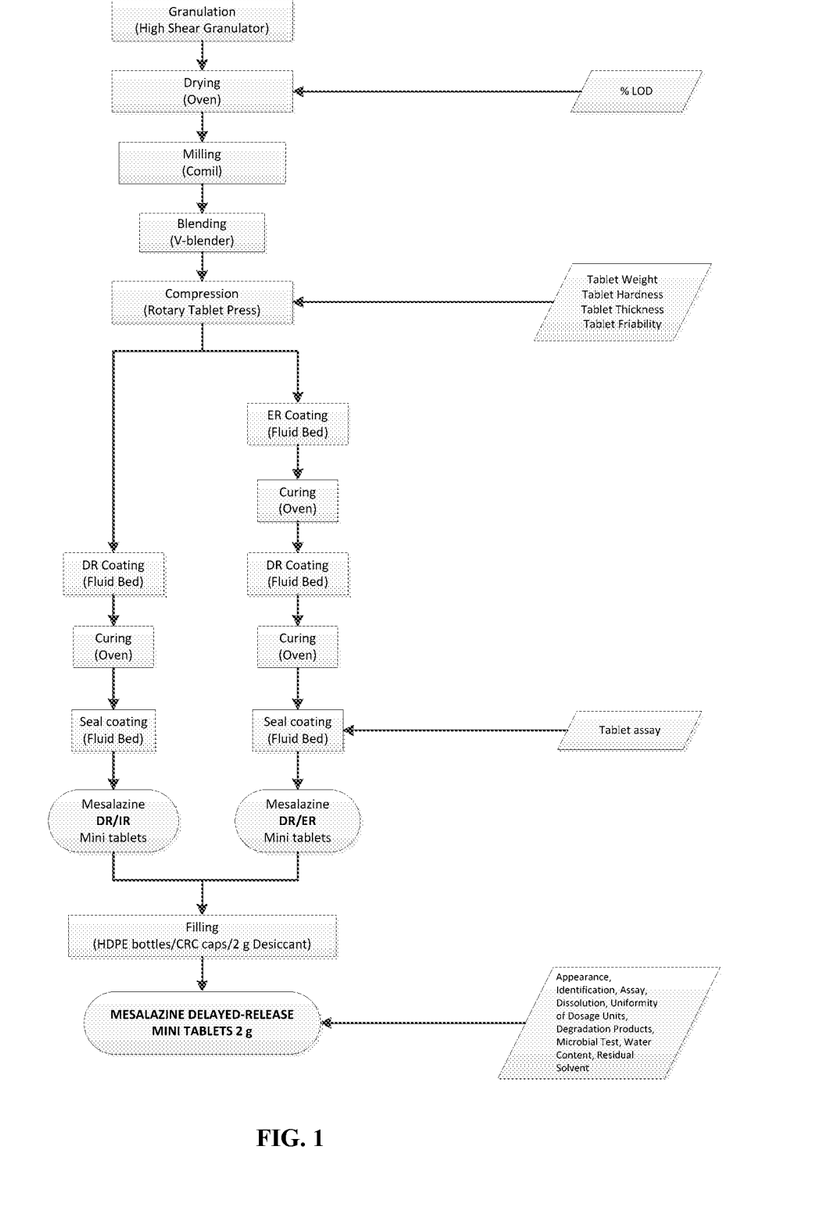
FIG. 1 is a general flow chart illustrating the manufacturing process for the manufacture of a unit dose pharmaceutical product as described herein.

In some embodiments illustrated in FIG. 1, minitablet matrices are made by a process wherein the mesalazine, a filler, and a binder are granulated, dried in an oven, and milled. The milled granules are then blended with a lubricant and then compressed into minitablet matrices of the desired weight, hardness, thickness, and friability.

To prepare DR/IR minitablets, in some embodiments, compressed minitablet matrices are coated with a pH-dependent enteric coating, and may be cured, such as in an oven. A seal coat may be applied to the cured DR/IR tablets.

To prepare DR/ER minitablets, in some embodiments compressed minitablet matrices are coated with a pH-independent extended release coating, and may be cured, such as in an oven. A pH-dependent enteric coating may be applied as an outer coating to the pH-independent coated minitablet matrices, which may be cured again, such as in an oven. A seal coat may be applied to the doubly-coated DR/ER minitablets.

Therapeutic Methods

Also provided herein are methods of administering mesalazine to a subject in need thereof, comprising orally administering to the subject a composition or unit dose pharmaceutical product as described herein. The subject may be suffering from or at risk of developing inflammatory bowel disease, including ulcerative colitis or Crohn's disease. The subject may be suffering from active inflammatory bowel disease or may be in remission. Thus, treating a subject includes reducing the symptoms and/or duration of active inflammatory bowel disease and increasing the length of remission periods (e.g., reducing the likelihood of flares).

As described above, oral administration of the compositions described herein provide delayed-immediate release (e.g., "burst" release) of mesalazine in the distal ileum and also provide extended release of mesalazine in the colon. While not wanting to be bound by theory, it is believed that subjects suffering from ulcerative colitis may particularly benefit from the methods described herein, since such subjects have more extensive disease (e.g., more extensive inflammation in the distal ileum and colon). Again, while not wanting to be bound by theory, subjects suffering from pancolitis or extensive colitis (e.g., occurring beyond the explenic flexure) and/or with backwash ileitis (e.g., inflammation of terminal ileum in ulcerative colitis) may particularly benefit from the methods described herein, e.g., from being treated by oral administration of compositions providing a "burst" release of mesalazine in the distal ileum and also extended release of mesalazine in the colon, since such patients would benefit from the local action of mesalazine at those sites.

While not wanting to be bound by theory, it also is believed that subjects suffering from Crohn's disease would benefit from the methods described herein, particularly those subjects suffering from ileal, ileocolonic or colonic disease.

Thus, also provided herein are methods of treating inflammatory bowel disease, including ulcerative colitis or Crohn's disease, comprising orally administering to a subject in need thereof a composition or unit dose pharmaceutical product as described herein. As noted above, a suitable subject may be suffering from one or more of ulcerative colitis, pancolitis, extensive colitis, backwash ileitis, and/or one or more of Crohn's disease, ileal disease, ileocolonic disease and colonic disease.

The methods may comprise administering a composition or unit dose pharmaceutical product as described herein one or more times per day, such as one, two, three, four, five, or more, times per day. In some embodiments, a unit dose pharmaceutical product is administered once a day. In some embodiments, a unit dose pharmaceutical product is administered twice a day. In some embodiments, a unit dose pharmaceutical product is administered three times a day. In some embodiments, a unit dose pharmaceutical product is administered four times a day. In some embodiments, a unit dose pharmaceutical product is administered five times a day.

EXAMPLES

The following specific examples are included as illustrative of the compositions and unit dose pharmaceutical products described herein. These examples are in no way intended to limit the scope of the disclosure. Other aspects of the disclosure will be apparent to those skilled in the art to which the disclosure pertains.

The following procedures can be used to produce compositions and unit dose pharmaceutical products described above.

Example 1: Delayed-Immediate Release Minitablets

The matrices for the minitablets can be made by granulating mesalazine and a carrier such as microcrystalline cellulose with a binder such as povidone (e.g., an aqueous solution of povidone), for example using a high-shear granulation process, and then drying the granules, such as in an oven, for example until loss on drying (LOD) is below 3.0%. The dried granules then can be milled and the milled granules can be blended with a lubricant such as magnesium stearate, such as by using a V-blender. The minitablets can then be formed by compressing the matrix blend, such as by using a rotary tablet press. These steps are illustrated in the top third of FIG. 1 and FIG. 2.

DR/IR minitablets can be made by coating the compressed minitablets, such as by using a fluid bed coater apparatus, using an enteric coating composition, such as a composition comprising a delayed-release coating (such as an aqueous suspension of Eudragit® L30D-55) containing a plasticizer such as dibutyl sebacate and an anti-tack agent such as talc, followed by curing. An optional seal coat can be applied onto the cured DR/IR minitablets, such as by using a fluid bed coater apparatus. These steps are illustrated in the left side of the middle third of FIG. 1 and FIG. 2.

Figure 3:
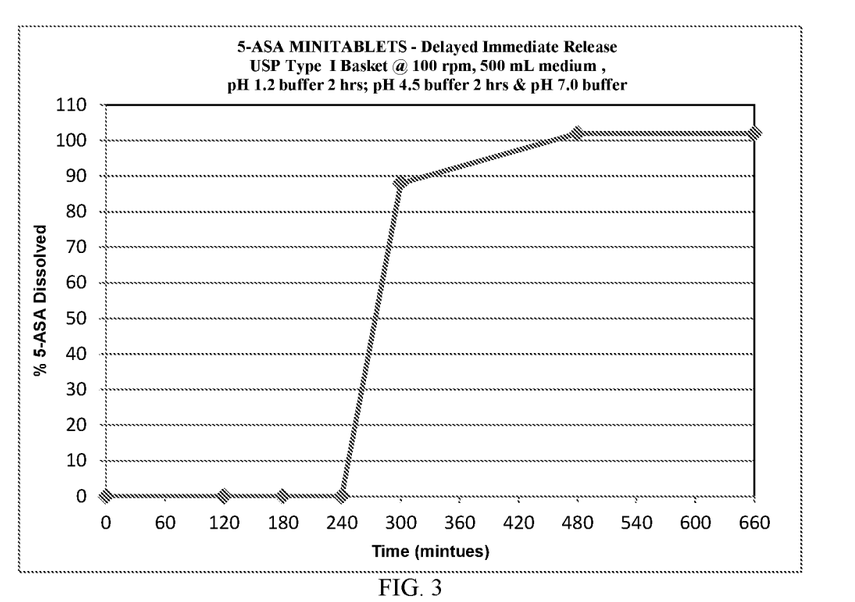
FIG. 3 is a graphical depiction of the dissolution profile of delayed-immediate release minitablets comprising mesalazine as described herein.

A release profile for DR/IR minitablets made in this manner is shown in FIG. 3.

Example 2: Delayed-Immediate Release Minitablets

Mesalazine minitablets matrices prepared as described in Example 1 can be used to prepare DR/IR minitablets by coating the compressed minitablets, such as by using a fluid bed coater apparatus, with an extended-release coating (such as an enteric coating composition comprising an aqueous suspension of hypromellose acetate succinate (AQOAT®)) containing a plasticizer such as triethyl citrate, an anti-tack agent such as talc and a lubricant/surfactant such as sodium lauryl sulfate.

Figure 4:
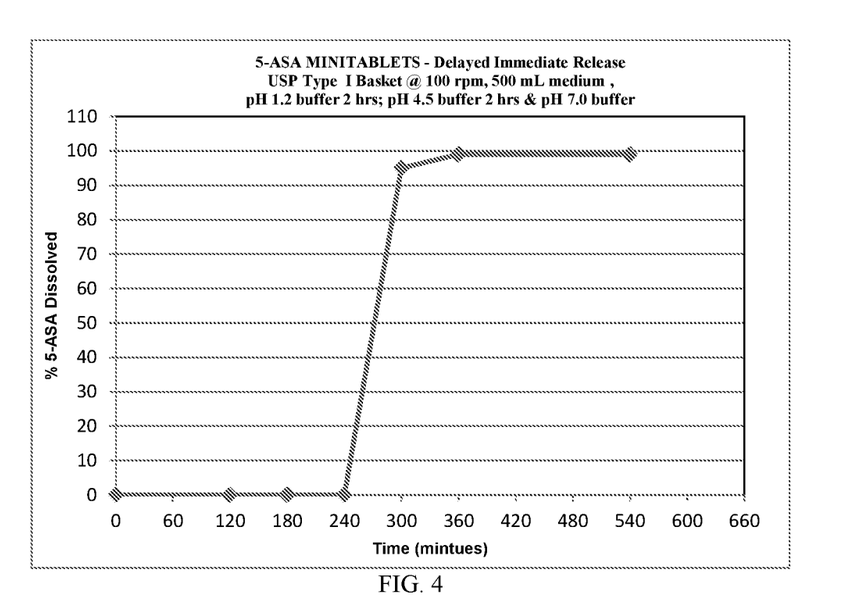
FIG. 4 is a graphical depiction of the dissolution profile of delayed-immediate release minitablets comprising mesalazine as described herein.

A release profile for DR/IR minitablets made in this manner is shown in FIG. 4.

Example 3: Delayed-Extended Release Minitablets

Mesalazine minitablets matrices prepared as described in Example 1 can be used to prepare DR/ER minitablets by coating the compressed minitablets, such as by using a fluid bed coater apparatus, with an extended release coating (such as a hydroalcoholic coating suspension containing ethylcellulose, hypromellose, triethyl citrate and talc), applied at a coating weight of approximately 3%. After curing, the ER-coated minitablets are further coated with a delayed-release coating, such as by using a fluid bed coater apparatus, with an aqueous dispersion of a delayed-release coating (such as a composition comprising Eudragit® FS30D and PlasACRYL™ T20), followed by curing. An optional seal coat can be applied onto the cured DR/ER minitablets, such as by using a fluid bed coater apparatus. These steps are illustrated in the right side of the middle third of FIG. 1 and FIG. 2.

Figure 5:
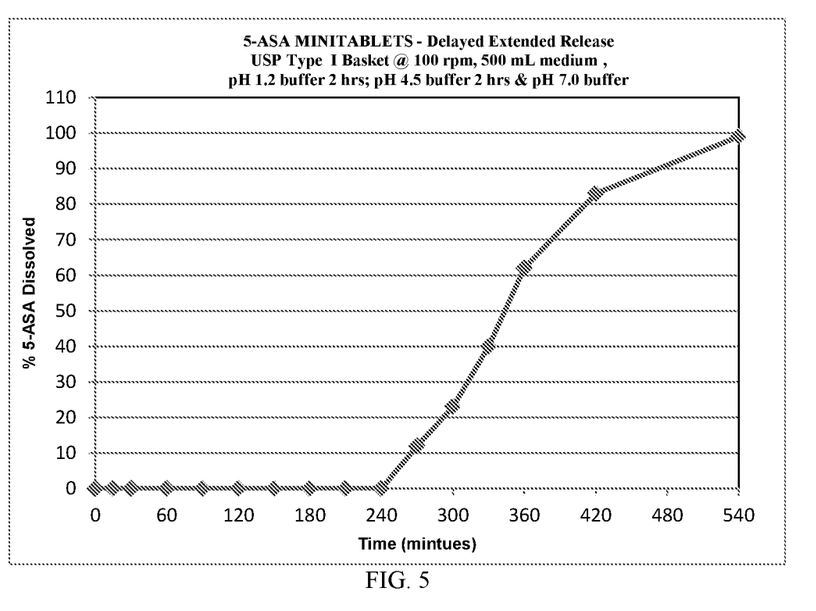
FIG. 5 is a graphical depiction of the dissolution profile of delayed-extended release minitablets comprising mesalazine as described herein.

A release profile for DR/ER minitablets made in this manner is shown in FIG. 5.

Example 4: Delayed-Extended Release Minitablets

DR/ER minitablets can be made as described above using as the extended release coating a hydroalcoholic coating suspension containing ethylcellulose, hypromellose, triethyl citrate and talc, applied at a coating weight of approximately 7.5%, and using as the delayed-release coating an aqueous dispersion of Eudragit® FS30D and PlasACRYL™ T20.

Figure 6:
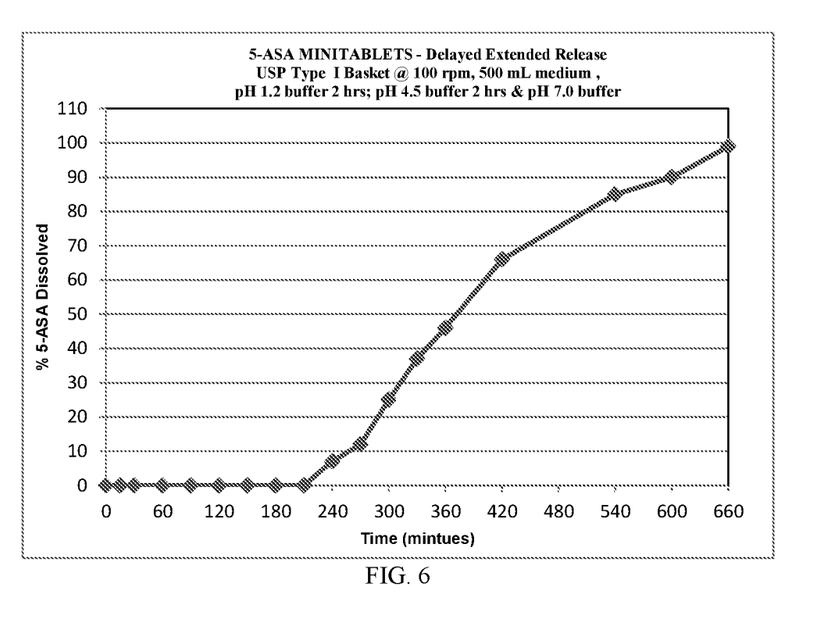
FIG. 6 is a graphical depiction of the dissolution profile of delayed-extended release minitablets comprising mesalazine as described herein.

A release profile for DR/ER minitablets made in this manner is shown in FIG. 6.

Example 5: Delayed-Extended Release Minitablets

DR/ER minitablets can be made as described above using as the extended release coating a hydroalcoholic coating suspension containing ethylcellulose, hypromellose, triethyl citrate and talc, applied at a coating weight of approximately 10%, and using as the delayed-release coating an aqueous dispersion of Eudragit® FS30D and PlasACRYL™ T20.

Figure 7:
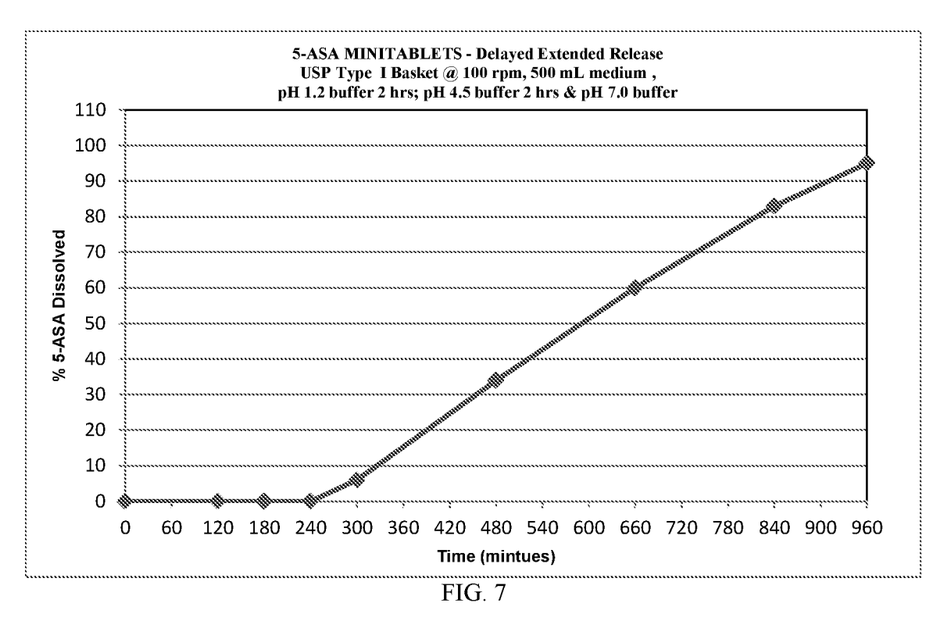
FIG. 7 is a graphical depiction of the dissolution profile of delayed-extended release minitablets comprising mesalazine as described herein.

A release profile for DR/ER minitablets made in this manner is shown in FIG. 7.

Example 6: Delayed-Extended Release Minitablets

DR/ER minitablets can be made as described above using as the extended release coating a hydroalcoholic coating suspension containing ethylcellulose and hypromellose, applied at a coating weight of approximately 3%, and using as the delayed-release coating an aqueous dispersion of Eudragit® FS30D and PlasACRYL™ T20.

Figure 8:
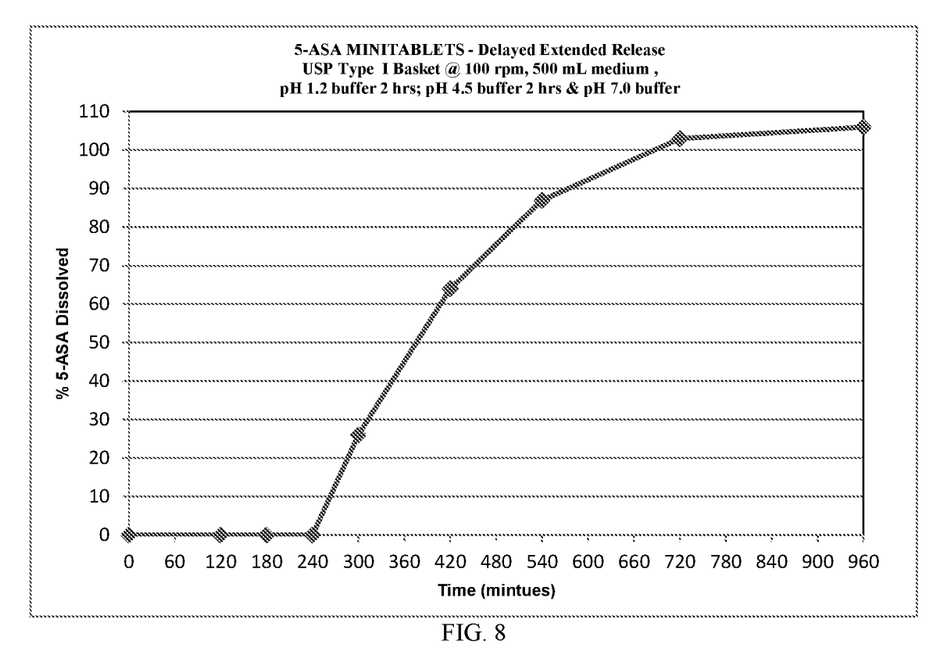
FIG. 8 is a graphical depiction of the dissolution profile of delayed-extended release minitablets comprising mesalazine as described herein.

A release profile for DR/ER minitablets made in this manner is shown in FIG. 8.

Example 7: Delayed-Extended Release Minitablets

DR/ER minitablets can be made as described above using as the extended release coating a hydroalcoholic coating suspension containing ethylcellulose and hypromellose, applied at a coating weight of approximately 5%, and using as the delayed-release coating an alcoholic solution of Eudragit® S 100 and triethyl citrate.

Figure 9:
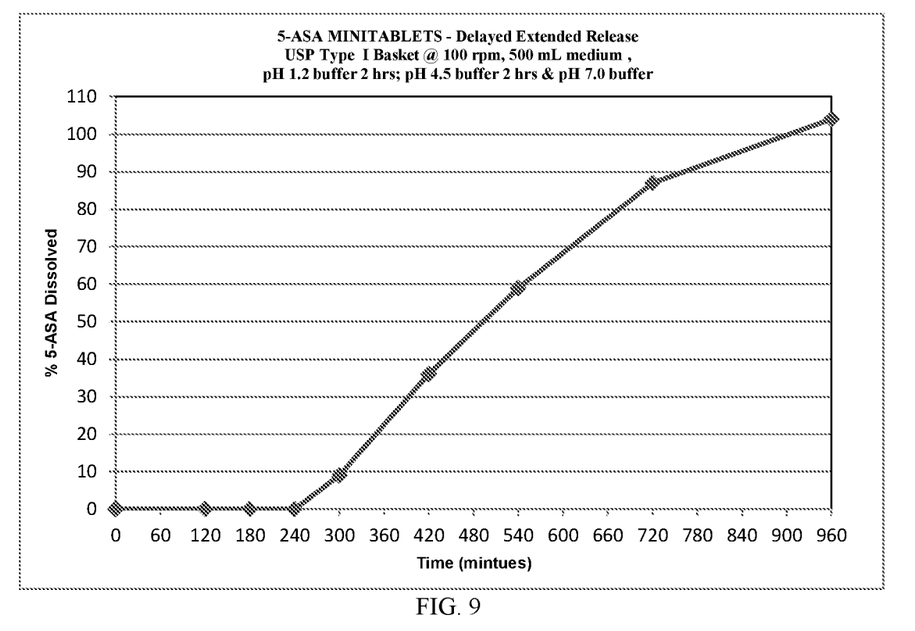
FIG. 9 is a graphical depiction of the dissolution profile of delayed-extended release minitablets comprising mesalazine as described herein.

A release profile for DR/ER minitablets made in this manner is shown in FIG. 9.

Example 8: DR/IR Minitablets+DR/ER Minitablets

Figure 10:
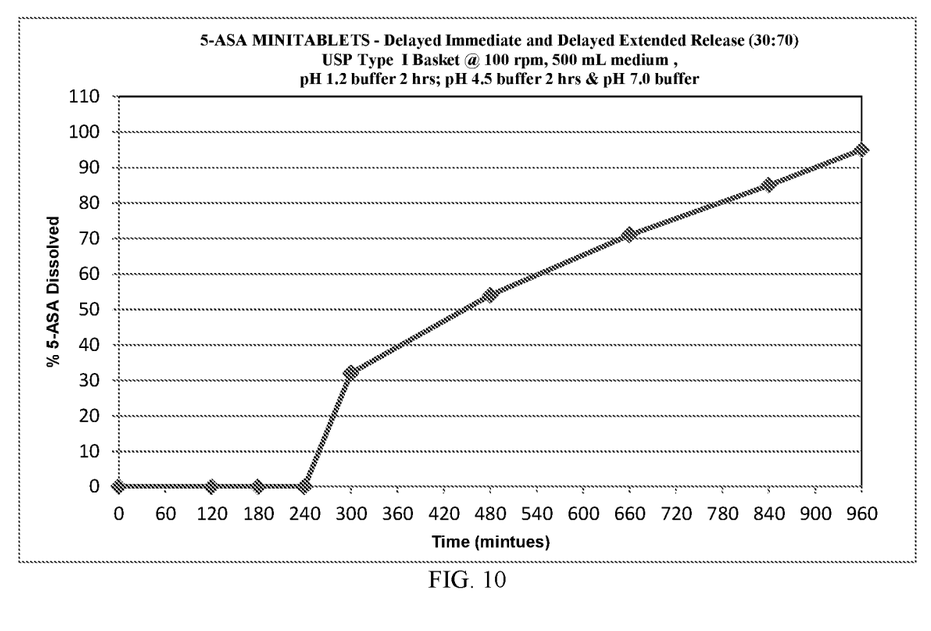
FIG. 10 is a graphical depiction of the dissolution profile of a combination product comprising delayed-extended release and delayed-immediate release minitablets comprising mesalazine as described herein.

DR/IR minitablets prepared as described in Example 1 and DR/ER minitablets prepared as described in Example 5 are combined in a 30:70 ratio. A release profile for the combination product is shown in FIG. 10.

Figure 2:
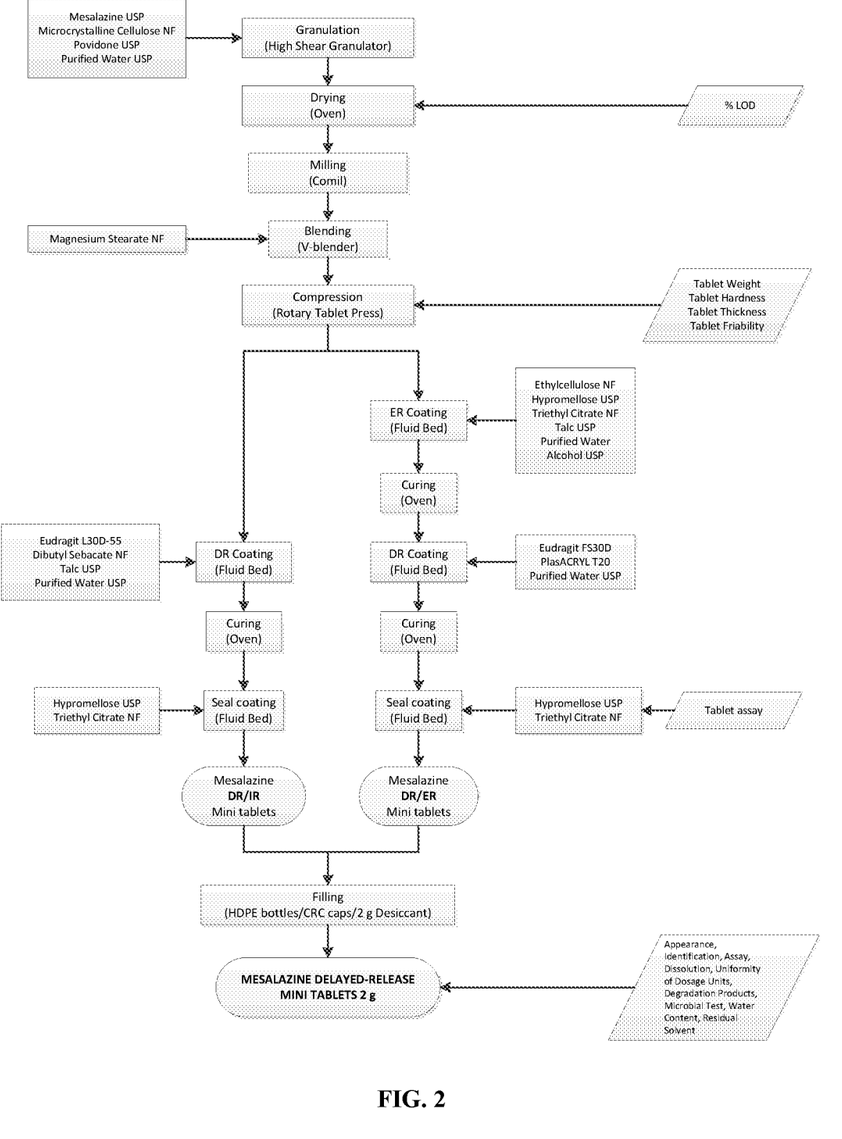
FIG. 2 is a flow chart illustrating the manufacturing process for the manufacture of a formulation of the unit dose pharmaceutical product as described herein.

To prepare a pharmaceutical product, the combined DR/IR and DR/ER minitablets can be filled into a container, as illustrated in the bottom third of FIG. 1 and FIG. 2. To prepare a unit dose pharmaceutical product, a unit dose of the combined DR/IR and DR/ER minitablets can be filled into a container.

Example 9: DR/IR Minitablets+DR/ER Minitablets

Figure 11:
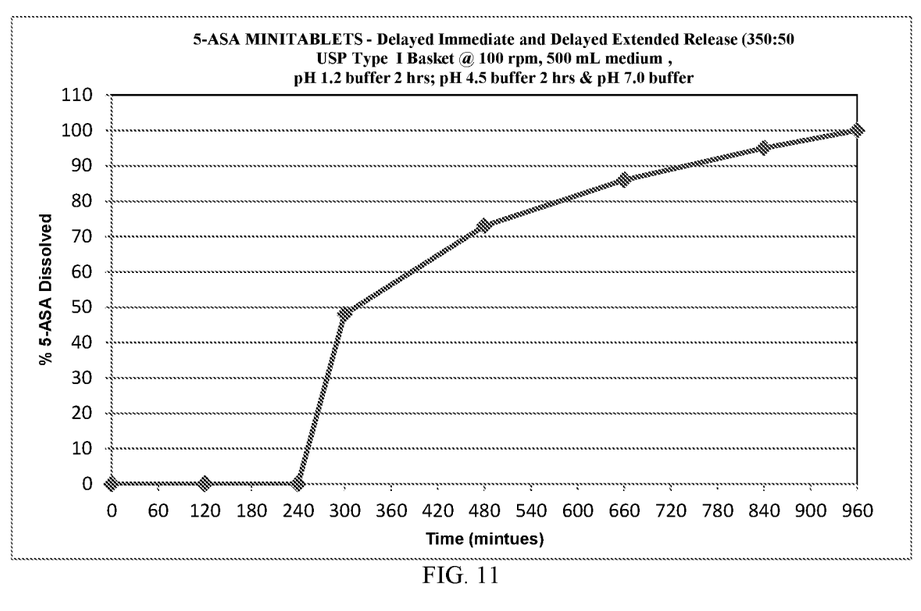
FIG. 11 is a graphical depiction of the dissolution profile of a combination product comprising delayed-extended release and delayed-immediate release minitablets comprising mesalazine as described herein.

DR/IR minitablets prepared as described in Example 1 and DR/ER minitablets prepared as described in Example 5 are combined in a 50:50 ratio. A release profile for the combination product is shown in FIG. 11. To prepare a pharmaceutical product, the combined DR/IR and DR/ER minitablets can be filled into a container, as illustrated in the bottom third of FIG. 1 and FIG. 2. To prepare a unit dose pharmaceutical product, a unit dose of the combined DR/IR and DR/ER minitablets can be filled into a container.

Example 10: DR/IR Minitablets+DR/ER Minitablets

Figure 12:
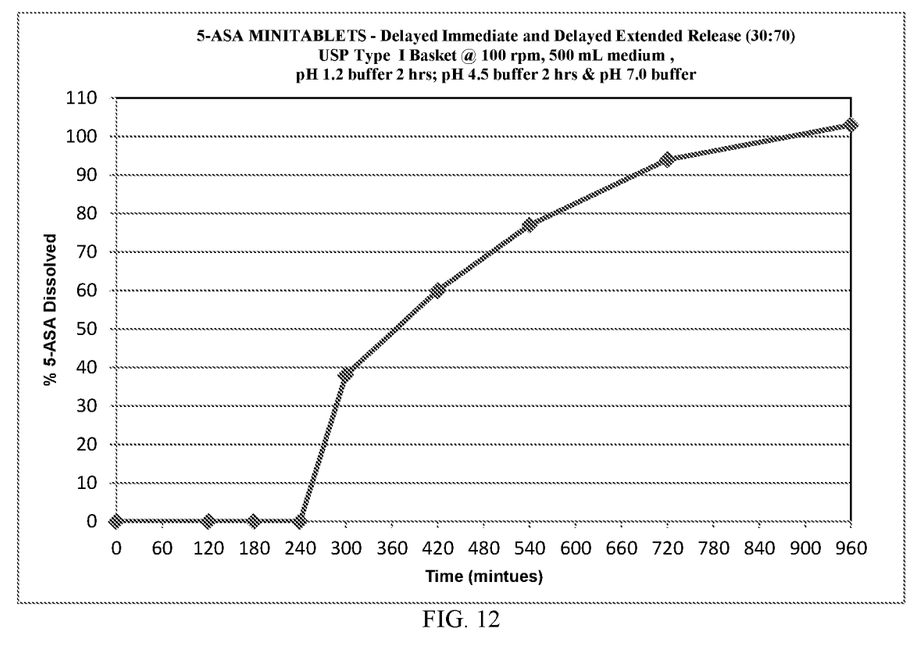
FIG. 12 is a graphical depiction of the dissolution profile of a combination product comprising delayed-extended release and delayed-immediate release minitablets comprising mesalazine as described herein.

DR/IR minitablets prepared as described in Example 1 and DR/ER minitablets prepared as described in Example 6 are combined in a 30:70 ratio. A release profile for the combination product is shown in FIG. 12.

Example 11: DR/IR Minitablets+DR/ER Minitablets

Figure 13:
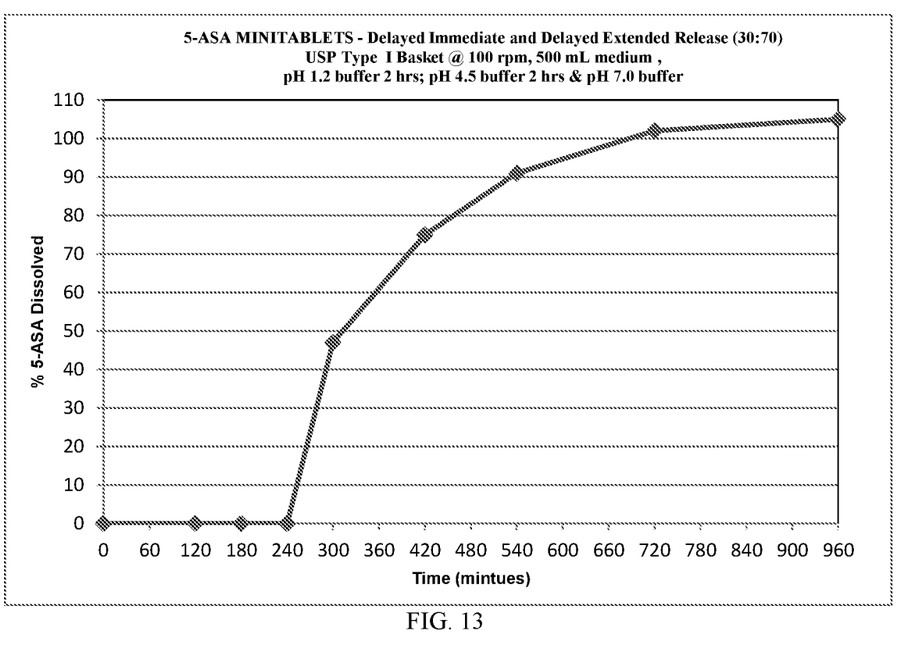
FIG. 13 is a graphical depiction of the dissolution profile of a combination product comprising delayed-extended release and delayed-immediate release minitablets comprising mesalazine as described herein.

DR/IR minitablets prepared as described in Example 1 and DR/ER minitablets prepared as described in Example 7 are combined in a 30:70 ratio. A release profile for the combination product is shown in FIG. 13.

What is claimed is:

1. A unit dose pharmaceutical product for the oral administration of mesalazine to a subject, comprising:
   (a) a plurality of delayed-immediate release minitablets comprising a compressed matrix comprising mesalazine provided with a pH-dependent enteric coating, wherein the delayed-immediate release minitablets selectively release mesalazine at a pH of about 5.5 or greater in the distal ileum; and
   (b) a plurality of delayed-extended release minitablets comprising a compressed matrix comprising mesalazine provided with an inner pH-independent extended release coating and an outer pH-dependent enteric coating, wherein the delayed-extended release minitablets selectively release mesalazine at a pH of about 7 or greater in the colon;
   wherein:
   the relative amounts of (a) and (b) in the unit dose pharmaceutical product are such that from 10 to 90% w/w of the mesalazine provided in the unit dose pharmaceutical is present in the delayed-extended release minitablets of (b);
   the total amount of mesalazine in the unit dose pharmaceutical product is from about 0.4 to 6 g.

2. The unit dose pharmaceutical product of claim 1, wherein, when subject to in vitro dissolution testing according to USP Type 1 Basket at 37° C. and 100 rpm in 500 mL dissolution medium of pH 1.2 buffer for 2 hours, followed by pH 4.5 buffer for 2 hours, followed by pH 7.0 buffer, the delayed-immediate release minitablets exhibit substantially no release of mesalazine at pH 1.2 and pH 4.5, and release substantially all mesalazine within 120 minutes at pH 7.0.

3. The unit dose pharmaceutical product of claim 1, wherein, when subject to in vitro dissolution testing according to USP Type 1 Basket at 37° C. and 100 rpm in 500 mL dissolution medium of pH 1.2 buffer for 2 hours, followed by pH 4.5 buffer for 2 hours, followed by pH 7.0, the delayed-immediate release minitablets exhibit substantially no release of mesalazine at pH 1.2 and pH 4.5, and release substantially all mesalazine within 90 minutes at pH 7.0.

4. The unit dose pharmaceutical product of claim 1, wherein the delayed-immediate release minitablets of (a) release at least 50% w/w of their total mesalazine content in the distal ileum.

5. The unit dose pharmaceutical product of claim 1, wherein the delayed-immediate release minitablets of (a) release at least 30% w/w of their total mesalazine content in the distal ileum.

6. The unit dose pharmaceutical product of claim 1, wherein, when subject to in vitro dissolution testing according to USP Type 1 Basket at 37° C. and 100 rpm in 500 mL dissolution medium of pH 1.2 buffer for 2 hours, followed by pH 4.5 buffer for 2 hours, followed by pH 7.0 buffer for 12 hours, the delayed-extended release minitablets exhibit substantially no release of mesalazine at pH 1.2 and pH 4.5, and exhibit extended release of mesalazine over at least 4 hours at pH 7.0.

7. The unit dose pharmaceutical product of claim 1, wherein, when subject to in vitro dissolution testing according to USP Type 1 Basket at 37° C. and 100 rpm in 500 mL dissolution medium of pH 1.2 buffer for 2 hours, followed by pH 4.5 buffer for 2 hours, followed by pH 7.0 buffer for 12 hours, the delayed-extended release minitablets exhibit substantially no release of mesalazine at pH 1.2 and pH 4.5, and exhibit extended release of mesalazine over at least 6 hours at pH 7.0.

8. The unit dose pharmaceutical product of claim 1, wherein, when subject to in vitro dissolution testing according to USP Type 1 Basket at 37° C. and 100 rpm in 500 mL dissolution medium of pH 1.2 buffer for 2 hours, followed by pH 4.5 buffer for 2 hours, followed by pH 7.0 buffer for 12 hours, the delayed-extended release minitablets exhibit substantially no release of mesalazine at pH 1.2 and pH 4.5, and exhibit extended release of mesalazine over at least 8 hours at pH 7.0.

9. The unit dose pharmaceutical product of claim 1, wherein, when subject to in vitro dissolution testing according to USP Type 1 Basket at 37° C. and 100 rpm in 500 mL dissolution medium of pH 1.2 buffer for 2 hours, followed by pH 4.5 buffer for 2 hours, followed by pH 7.0 buffer for 12 hours, the delayed-extended release minitablets exhibit substantially no release of mesalazine at pH 1.2 and pH 4.5, and exhibit extended release of mesalazine over at least 12 hours at pH 7.0.

10. The unit dose pharmaceutical product of claim 1, wherein the delayed-extended release minitablets of (b) release at least 50% w/w of their total mesalazine content in the colon.

11. The unit dose pharmaceutical product of claim 1, wherein the delayed-extended release minitablets of (b) release at least 70% w/w of their total mesalazine content in the colon.

12. The unit dose pharmaceutical product of claim 1, wherein the total amount of mesalazine in the unit dose pharmaceutical product is about 2 g or about 4 g.

13. The unit dose pharmaceutical product of claim 1, wherein the compressed matrix of (a) and the compressed matrix of (b) comprise at least 85% w/w mesalazine and, optionally, one or more selected from a pharmaceutically acceptable binder, a pharmaceutically acceptable filler, and a pharmaceutically acceptable lubricant.

14. The unit dose pharmaceutical product of claim 1, wherein the compressed matrix of (a) and the compressed matrix of (b) comprise micronized mesalazine.

15. The unit dose pharmaceutical product of claim 14, wherein the micronized mesalazine has a particle size distribution such that the $90^{th}$ percentile, D(v,0.9), is no more than 30 μm or such that D(v,0.9) is about 16-17 μm.

16. The unit dose pharmaceutical product of claim 1, wherein:
the compressed matrix of (a) and the compressed matrix of (b) each comprise mesalazine, povidone, microcrystalline cellulose, and magnesium stearate,
the pH-dependent enteric coating of (a) comprises one or more polymers selected from the group consisting of methacrylic acid and ethyl acrylate copolymer 1:1, hypromellose acetate succinate, and hypromellose phthalate,
the pH-dependent enteric coating of (b) comprises one or more polymers selected from the group consisting of methacrylic acid and methyl methacrylate copolymer 1:2, poly(methyl acrylate-co-methyl methacrylate-co-methacrylic acid) [7:3:1] and hypromellose acetate succinate, and
the pH-independent extended release coating of (b) comprises ethyl cellulose and hydroxypropyl methylcellulose.

17. The unit dose pharmaceutical product of claim 1, wherein the minitablets of (a) and/or the minitablets of (b) further comprise a seal coat exterior to the pH-dependent enteric coating.

18. The unit dose pharmaceutical product of claim 1, wherein the minitablets of (a) and the minitablets of (b) have a longest diameter of 1-4 mm or a length of 1-4 mm.

19. The unit dose pharmaceutical product of claim 1, wherein the minitablets of (a) and the minitablets of (b) are provided in a sachet, capsule, or vial.

20. A method of administering mesalazine to a subject in need thereof, comprising orally administering to the subject a unit dose pharmaceutical product according to claim 1.

21. A method of treating inflammatory bowel disease, comprising orally administering to the subject a unit dose pharmaceutical product according to claim 1.

22. A method of making a unit dose pharmaceutical product according to claim 1, comprising:
(a) forming a plurality of delayed-immediate release minitablets (a);
(b) forming a plurality of delayed-extended release minitablets (b); and
(c) providing (a) and (b) in a sachet, capsule, or vial, thereby obtaining the unit dose pharmaceutical product,
wherein the relative amounts of (a) and (b) in the unit dose pharmaceutical product are such that from 10 to 90% w/w of the mesalazine provided in the unit dose pharmaceutical is present in the delayed-extended release minitablets of (b), and the total amount of mesalazine in the unit dose pharmaceutical product is from about 0.4 to 6 g.

* * * * *

UNITED STATES PATENT AND TRADEMARK OFFICE
CERTIFICATE OF CORRECTION

| | |
|---|---|
| PATENT NO. | : 10,874,617 B2 |
| APPLICATION NO. | : 16/094644 |
| DATED | : December 29, 2020 |
| INVENTOR(S) | : Liang et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 19 days.

Signed and Sealed this
Thirty-first Day of January, 2023

Katherine Kelly Vidal
*Director of the United States Patent and Trademark Office*